United States Patent
Zambounis et al.

[11] Patent Number: 5,840,449
[45] Date of Patent: Nov. 24, 1998

[54] STRUCTURED PIGMENT COATING AND ITS PREPARATION AND USE

[75] Inventors: John Zambounis, Basel; Manfred Hofmann, Marly, both of Switzerland

[73] Assignee: Ciba Specialty Chemicals Corporation, Tarrytown, N.Y.

[21] Appl. No.: 643,723

[22] Filed: May 6, 1996

[30] Foreign Application Priority Data

May 12, 1995 [CH] Switzerland .............................. 1394/95

[51] Int. Cl.⁶ .............................. G02B 5/20; G11B 7/00; G11B 7/26; B05D 3/00
[52] U.S. Cl. .................. 430/7; 430/270.15; 430/270.16; 430/332.333; 430/338; 430/21; 430/945; 427/545; 427/555; 427/557; 427/162; 427/532
[58] Field of Search ................................. 430/7, 270.15, 430/270.16, 332, 333, 338, 21, 945; 427/545, 555, 557, 162, 532

[56] References Cited

U.S. PATENT DOCUMENTS

| | | | |
|---|---|---|---|
| 3,754,921 | 8/1973 | Riester | 430/338 |
| 5,144,333 | 9/1992 | Mizuguchi et al. | 346/1.1 |
| 5,221,751 | 6/1993 | Acker et al. | 548/455 |
| 5,316,852 | 5/1994 | Mizuguchi et al. | 428/411.1 |
| 5,352,551 | 10/1994 | Mizuguchi et al. | 430/17 |
| 5,484,943 | 1/1996 | Zambounis et al. | 548/453 |

FOREIGN PATENT DOCUMENTS

| | | |
|---|---|---|
| 516435 | 6/1953 | Belgium . |
| 557851 | 11/1957 | Belgium . |
| 2117860 | 4/1995 | Canada . |
| 0401791 | 12/1990 | European Pat. Off. . |
| 0459201 | 12/1991 | European Pat. Off. . |
| 0490817 | 6/1992 | European Pat. Off. . |
| 0530145 | 3/1993 | European Pat. Off. . |
| 0615233 | 9/1994 | European Pat. Off. . |
| 0648770 | 4/1995 | European Pat. Off. . |
| 0648817 | 4/1995 | European Pat. Off. . |

OTHER PUBLICATIONS

Angew. Chem. 68, 133–168 (1956).
G. Org. Chem. 22, 127–132 (1957).
Optical Recording 360–371 A.B. Marchant, Addison–Wesley 1990.
Thin Film Processes, W. Kern & L. Vossen (1978), Table of Contents Only.
Chem. Abst. 88–180036/26 of JP 118,098 (May 1988).
S Soc. Dyers & Col. 106/11,367 (1990).

*Primary Examiner*—John A. McPherson
*Attorney, Agent, or Firm*—Kevin T. Mansfield; Jacob M. Levine

[57] ABSTRACT

The present invention provides a process for the preparation of a material comprising a substrate on whose surface there is at least one pigment coating consisting of one or more pigments of the formula (I) or (II) or derivatives thereof $$A(D_1)(D_2)_x \quad (I)$$

$$Pc \quad (II)$$

in which

A is the radical of a chromophore of the quinacridone, anthraquinone, perylene, indigo, azo, quinophthalone, isoindolinone, isoindoline, dioxazine, phthalocyanine or diketopyrrolopyrrole series which contains nitrogen atoms attached to $D_1$ and to x $D_2$, each nitrogen atom present in A being able independently of the others to be attached to 0, 1 or 2 groups $D_1$ or $D_2$, $D_1$ and $D_2$ are hydrogen, x is an integer from 0 to 4, and Pc is a chromophore of the phthalocyanine series, which is applied by (a) coating the substrate with a solution or melt of at least one latent pigment of the formula (II) or (IV), $$A(D_3)(D_4)_x \quad (III)$$

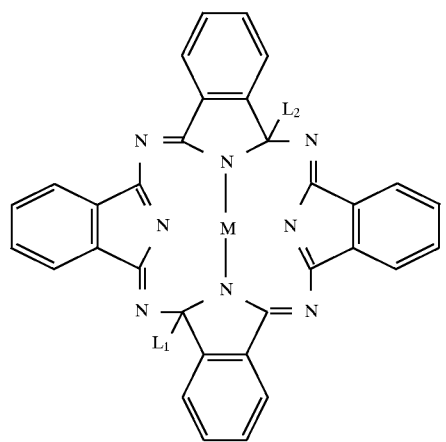

(IV)

and (b) converting the latent pigment partially or completely into its insoluble pigment form by eliminating groups $D_3$ and $D_4$, or by eliminating groups $L_1$ and $L_2$.

The invention also relates to a structured material prepared in this way, to its use as a color filter or for the permanent storage of digital information, and to a method of reading out digital information stored thereon by irradiation with a light source and measurement of the intensity of the reflected or transmitted light beam.

24 Claims, No Drawings

STRUCTURED PIGMENT COATING AND ITS PREPARATION AND USE

The present invention relates to a process for the preparation of a material comprising a substrate and a pigment coating which is produced using soluble pigment precursors, to certain materials prepared by the process, and to the use thereof as colour filters or for the permanent storage of digital information.

It is known from EP 648 770, EP 648 817, Angewandte Chemie 68/4, 133–150 (1956) and also J. Org. Chem. 22, 127–132 (1957) that organic pigments can be converted into soluble derivatives which are of other colours. These derivatives comprise fluorescent dyes, or comprise vat dyes, whose properties are, however, undesirable for numerous colouring purposes, examples being their poor light stability, high migration tendency, low melting point or fluorescence. Dyes of this kind dissolved in a substrate can be converted back to the initial pigments or can be converted into pigments with different crystal modifications.

High-grade pigments, in contrast, possess great light stability and dissolve only to a very minor extent or not at all in the substrate to be coloured. Although organic pigments can, in accordance with A. B. Marchant, "Optical Recording", 360–371 (Addison-Wesley Publ. Co., 1990), W. Kern & L. Vossen, "Thin Film Processes" (1978) and JP-88/118098, be sublimed (applied by vapour deposition) directly onto substrates, their limited thermal stability means that a high vacuum is usually necessary in order to do so [H. Nakazumi et al., J. Soc. Dyers +Col. 106/11, 367 (1990)].

Sublimation, therefore, is a very slow, laborious and uneconomic coating technique which is unsuitable for the efficient mass production of pigmented products. Moreover, it is difficult to control the crystal growth, so that coatings obtained by sublimation often include pigment particles of an unwanted size or are not homogeneously and uniformly coloured to the desired extent. The sublimation method cannot be used to produce high-resolution patterns, and there is the problem of pigment particles which have become deposited at unwanted locations on the substrate or the apparatus.

As a consequence, pigments are almost always used only for mass colouring, i.e. they are simply dispersed in an appropriate substrate, for example in plastics granules, films or fibres, in coating formulations or in printing inks. In the context of mass colouring, however, disadvantages occur, such as rheological problems, especially in the case of very fine pigment particles, negative effects of the pigments on the light stability of the substrate, or unsatisfactory pigment stability in connection with the nature of the substrate.

Furthermore, homogeneous pigmentation requires long dispersion of the organic pigment with high shear energy and/or at high temperature. This can take place either directly, during incorporation into the substrate, or even beforehand, as with the manufacture of pigment preparations or masterbatches.

Furthermore, in mass colouring, depending on the intended use and desired result, it is necessary to have recourse to different pigment variants of a given chromophore, such as a transparent or opaque form, different surface treatments or different crystal modifications. The result of this is unnecessary and uneconomic broadening of the range which must be held in stock.

When a binder is used, moreover, the precursors included therein can undergo unwanted reaction over time to form coloured products.

It has therefore not hitherto been possible to satisfy the need for a simple coating method without the use of binders.

The present invention now provides a process for the preparation of a material comprising a substrate on whose surface there is at least one pigment coating consisting of one or more pigments of the formula (I) or (II) or derivatives thereof

  (I)

  (II)

in which

A is the radical of a chromophore of the quinacridone, anthraquinone, perylene, indigo, azo, quinophthalone, isoindolinone, isoindoline, dioxazine, phthalocyanine or diketopyrrolopyrrole series which contains nitrogen atoms attached to $D_1$ and to x $D_2$, each nitrogen atom present in A being able independently of the others to be attached to 0, 1 or 2 groups $D_1$ or $D_2$, $D_1$ and $D_2$ are hydrogen, x is an integer from 0 to 4, and Pc is a chromophore of the phthalocyanine series, which is applied by (a) coating the substrate with a solution or melt of at least one latent pigment of the formula (III),

  (III)

or of a derivative thereof,
or at least one latent pigment of the formula (IV)

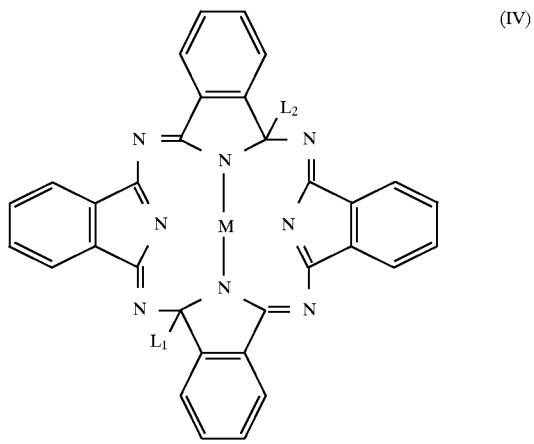  (IV)

or of a derivative or a positional isomer thereof,

A and x in formula (III) having the same meaning as in formula (I), A containing nitrogen atoms attached to $D_3$ and to x $D_4$, and each nitrogen atom present in A being able independently of the others to be attached to 0, 1 or 2 groups $D_3$ or $D_4$, and $D_3$ and $D_4$ independently of one another being groups of the formula

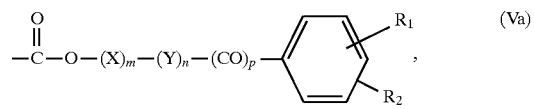  (Va)

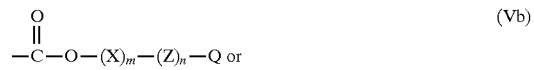  (Vb)

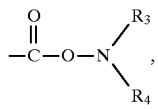 (Vc)

and in formula (IV) $L_1$ and $L_2$ independently of one another are halogen, $C_1-C_{18}$alkoxy, $C_2-C_{18}$dialkylamino, $C_1-C_{18}$cycloalkylamino, $C_1-C_6$alkylpiperidino or morpholino, and M is two hydrogens or an at least divalent metal atom, and (b) converting the latent pigment partially or completely into its insoluble pigment form by eliminating groups $D_3$ and $D_4$ and replacing them by hydrogen, or by eliminating groups $L_1$ and $L_2$, where, in the formulae (Va), (Vb) and (Vc), m, n and p independently of one another are 0 or 1, X is $C_1-C_{14}$alkylene, $C_2-C_{14}$alkenylene, $C_2-C_{14}$alkynylene, $C_4-C_{12}$cycloalkylene or $C_4-C_{12}$cycloalkenylene, Y is a group —V—$(CH_2)_q$—, Z is a group —V—$(CH_2)_r$—, V is $C_3-C_6$cycloalkylene, q is a number from 1 to 6 and r is a number from 0 to 6, $R_1$ and $R_2$ independently of one another are hydrogen, $C_1-C_6$alkyl, $C_1-C_4$alkoxy, halogen, CN, $NO_2$, phenyl which is unsubstituted or substituted by $C_1-C_4$alkyl, $C_1-C_4$alkoxy or halogen, or are phenoxy, Q is hydrogen, CN, $Si(R_1)_3$, a group $C(R_5)(R_6)(R_7)$, in which $R_5$, $R_6$ and $R_7$ independently of one another are hydrogen or halogen and at least one of the radicals $R_5$, $R_6$ and $R_7$ is halogen,

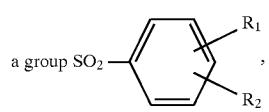

in which $R_1$ and $R_2$ are as defined above, a group $SO_2R_8$ or $SR_8$, in which $R_8$ is $C_1-C_4$alkyl, a group $CH(R_9)_2$, in which $R_9$ is phenyl which is unsubstituted or substituted by $C_1-C_4$alkyl, $C_1-C_4$alkoxy or halogen, or a group of the formula

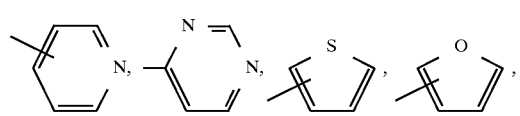

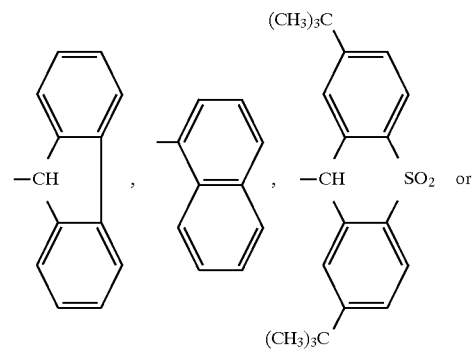

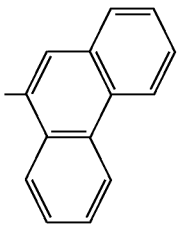

and $R_3$ and $R_4$ independently of one another are hydrogen, $C_1-C_{18}$alkyl, or a group

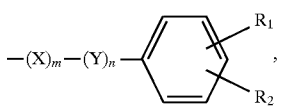

in which X, Y, $R_1$, $R_2$, m and n are as defined above, or $R_3$ and $R_4$ together with the nitrogen atom to which they are attached form a pyrrolidinyl, piperidyl or morpholinyl radical.

In the dye radical A, each nitrogen atom attached to groups $D_1$, $D_2$, $D_3$ or $D_4$ is preferably directly adjacent to at least one carbonyl group, or each of these nitrogen atoms is conjugated with a carbonyl group. It is not necessary, and often not appropriate, for all nitrogen atoms of a dye radical to be attached to groups $D_1$, $D_2$, $D_3$ or $D_4$; rather, $A(D_1)(D_2)_x$ and $A(D_3)(D_4)_x$ can, if desired, contain further

=N—, —NH— or —$NH_2$ groups within the radical A.

In contrast, more than one group $D_1$, $D_2$, $D_3$ or $D_4$ can be attached to a single nitrogen atom, for example two if the chromophore contains a group —$NH_2$, so that the radical A thereof may be either —NH' or —N.

A is the radical of known chromophores having the basic structure

for example

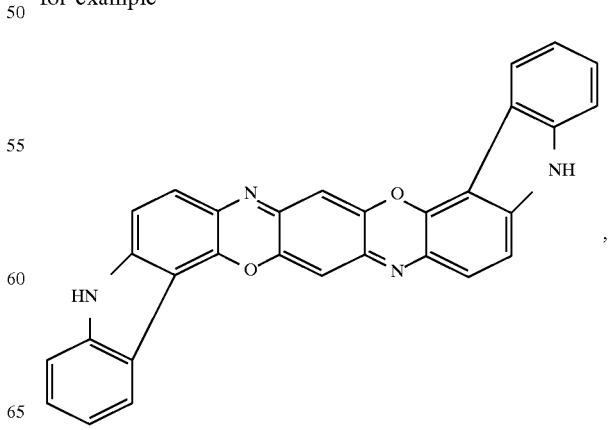

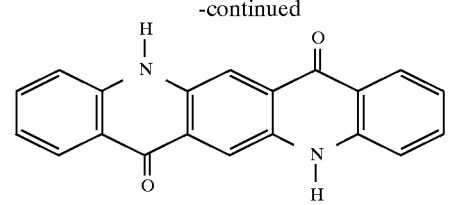
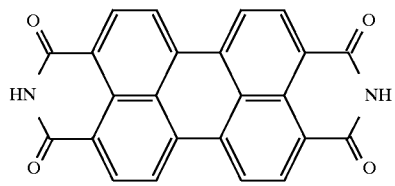
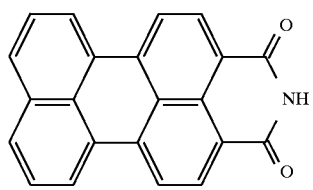
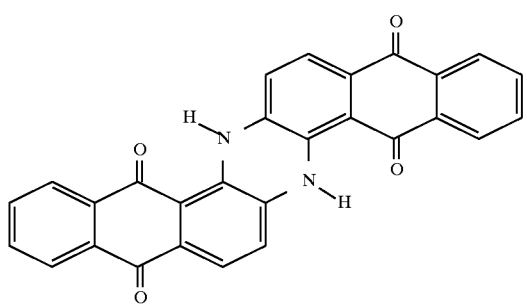
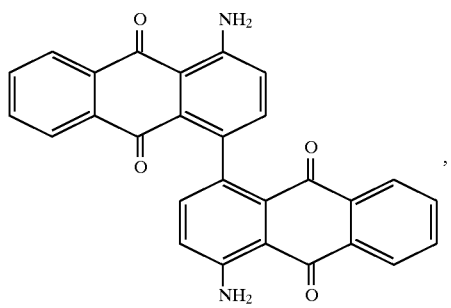
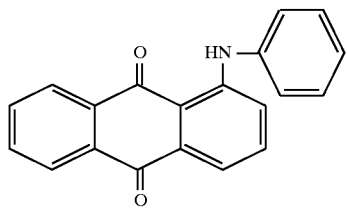
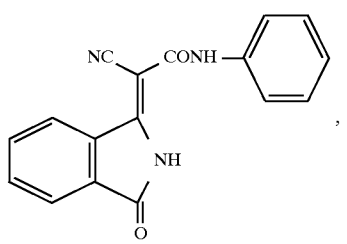
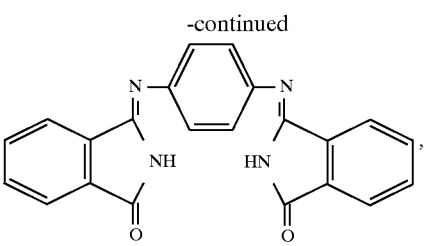
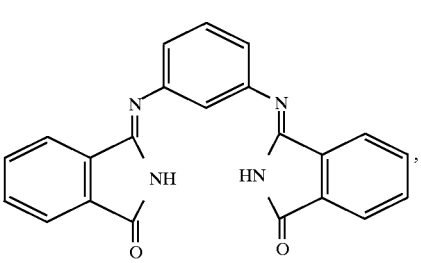
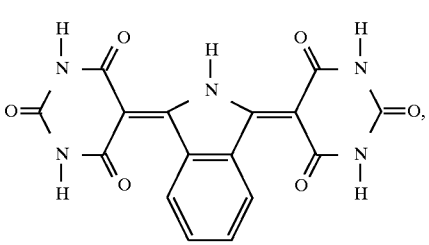
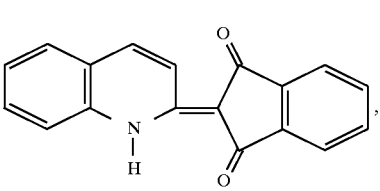
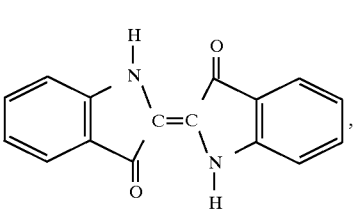
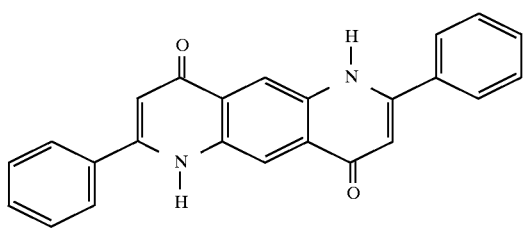
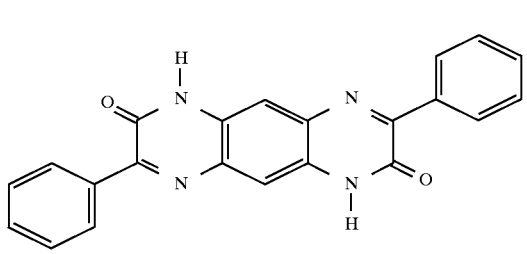

-continued

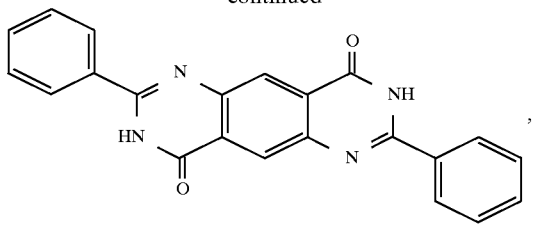

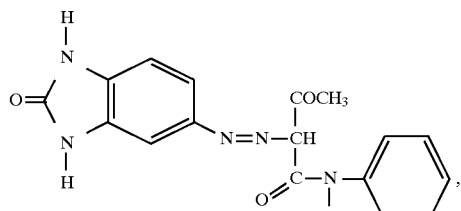

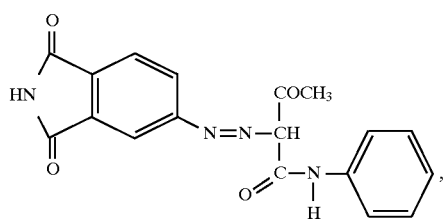

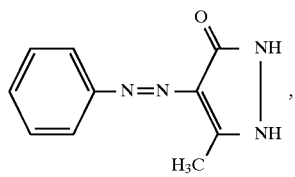

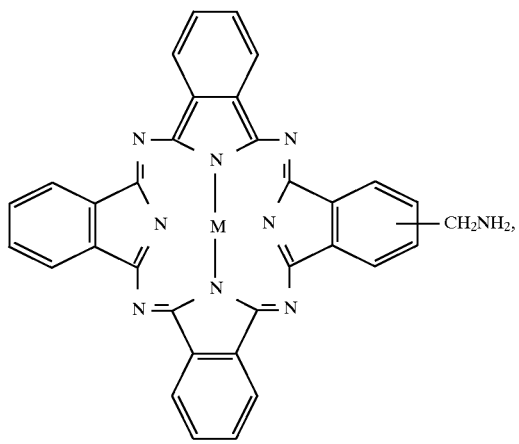

in which M is as defined above, or

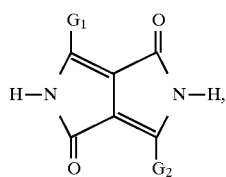

in which $G_1$ and $G_2$ independently of one another are a group of the formula

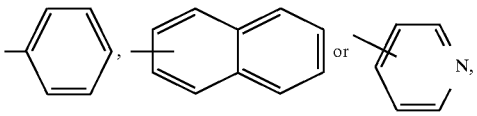

or, for each structure, any known derivative thereof.

Pc is a phthalocyanine of the basic structure

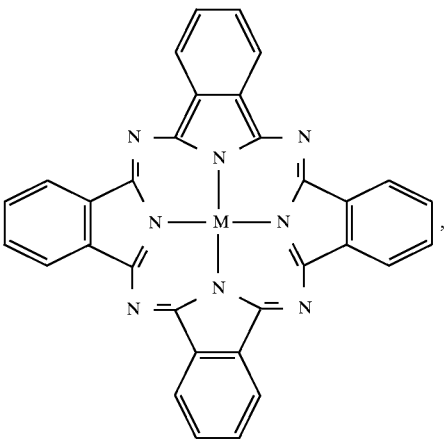

in which M is, for example, $H_2$, Mg, Ca, Ti, V, Mn, Fe, Co, Ni, Cu, Zn, Zr, Pd, Cd, Sn, Ce, Hg, Pb or Bi, especially a divalent metal, or any known derivative thereof.

Examples of possible derivatives are mono- or polysubstituted chromophores of the basic structures given above, and, especially in the case of phthalocyanines, those in which the metal is in the form of metal oxide, metal salt or metal complex, for example —Ti(O)—, —V(O)—, —Fe(OH)— or —[Co$^+$(NH$_3$)$_2$]Cl$^-$—. If desired, the substituents on the carbon framework may, for example, be—attached via a direct bond or via carbonyl, carbonyloxy, oxycarbonyl, sulfonyl or sulfinyl—halogen, nitro, amino, hydroxyl, $C_1$–$C_{18}$alkyl, $C_5$–$C_6$cycloalkyl, $C_1$–$C_4$alkoxy, $C_1$–$C_{18}$alkylthio, $C_1$–$C_{18}$alkylamino, $C_2$–$C_{18}$dialkylamino or $C_1$–$C_{18}$cycloalkylamino.

$C_1$–$C_{14}$alkylene or $C_4$–$C_{12}$cycloalkylene X is a straight-chain or branched alkylene or cycloalkylene, for example methylene, dimethylene, trimethylene, 1-methylmethylene, 1,1-dimethylmethylene, 1-ethyldimethylene, 1,1-dimethyldimethylene, 1-ethyl-1-methyl-dimethylene, 1,1-dimethyltrimethylene, 2,2-dimethyltrimethylene, tetramethylene, 1,1-dimethyltetramethylene, hexamethylene, decamethylene, 1,1-dimethyldecamethylene, 1,1-diethyidecamethylene, tetradecamethylene, 1,2-cyclobutylene, 1,2-cyclopentylene, 1,2-cyclohexylene, 1,4-cyclohexylene or 2,2,6-trimethyl-1,4-cyclohexylene.

X as $C_2$–$C_{14}$alkenylene, $C_2$–$C_{14}$alkynylene or $C_4$–$C_{12}$cycloalkenylene is straight-chain or branched alkenylene, alkynylene or cycloalkenylene, for example vinylene, allylene, methallylene, 1-methyl-2-butenylene, 1,1-dimethyl-3-butenylene, 2-butenylene, 2-hexenylene, 3-hexenylene, 1-methyl-2,6-but-3-ynylene or 1,4-cyclohexylene.

Any halogen substituents are, for example, iodine or fluorine, especially bromine and preferably chlorine.

$C_1$–$C_6$alkyl is, for example, methyl, ethyl, n-propyl, isopropyl, n-butyl, sec-butyl, tert-butyl, n-amyl, tert-amyl or hexyl and, in the case of $C_1$–$C_{18}$alkyl, additional examples are heptyl, octyl, 2-ethylhexyl, nonyl, decyl, dodecyl, tetradecyl, hexadecyl and otadecyl.

$C_5$–$C_6$cycloalkyl is, for example, cyclopentyl and, in particular, cyclohexyl.

$C_3$–$C_6$cycloalkylene is, for example, cyclopropylene, cyclobutylene, cyclopentylene and, in particular, cyclohexylene.

$C_1$–$C_4$alkoxy is, for example, methoxy, ethoxy, n-propoxy, isopropoxy or butyloxy, and $C_1$–$C_{18}$alkoxy is in addition hexyloxy, decyloxy, dodecyloxy, hexadecyloxy or octadecyloxy, for example.

$C_1$–$C_{18}$alkylthio is, for example, methylthio, ethylthio, propylthio, butylthio, octylthio, decylthio, hexadecylthio or octadecylthio.

$C_1$–$C_{18}$alkylamino is, for example, methylamino, ethylamino, propylamino, hexylamino, decylamino, hexadecylamino or octadecylamino.

$C_2$–$C_{18}$dialkylamino is, for example, dimethylamino, diethylamino, methylpropylamino, ethylhexylamino, methyidecylamino, dioctylamino or ethylhexadecylamino, the carbon atoms of both alkyl radicals being counted together.

$C_1$–$C_{18}$cycloalkylamino is, for example, pyrrolidino, piperidino, methylpyrrolidino, methylpiperidino, dimethylpyrrolidino, dimethylpiperidino, dodecylpyrrolidino, dodecylpiperidino, preferably piperidino, 4-methylpiperidino, 4-ethylpiperidino, 4-propylpiperidino and 4-butylpiperidino.

Particular interest attaches to the process set out above in which latent pigments of the formula (III) are used in which x is 0 or 1 and $D_3$ and $D_4$ independently of one another are groups of the formula

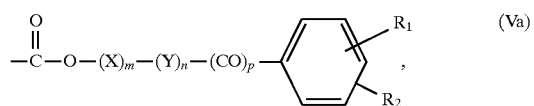 (Va)

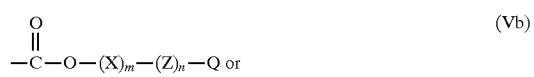 (Vb)

 (Vc)

n and p are both 0, m is 0 or 1,

Q is hydrogen, CN, $CCl_3$,

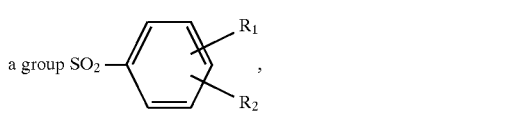

$SO_2CH_3$ or $SCH_3$,

X is $C_1$–$C_4$alkylene or $C_2$–$C_5$alkenylene, $R_1$ and $R_2$ independently of one another are hydrogen, $C_1$–$C_4$alkyl, methoxy, chlorine or $NO_2$, and $R_3$ and $R_4$ independently of one another are hydrogen, $C_1$–$C_4$alkyl or

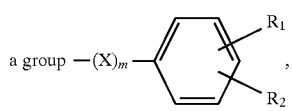

or $R_3$ and $R_4$ together form a piperidyl radical, and especially those in which x is 1 and $D_3$ and $D_4$ are identical and are groups of the formula

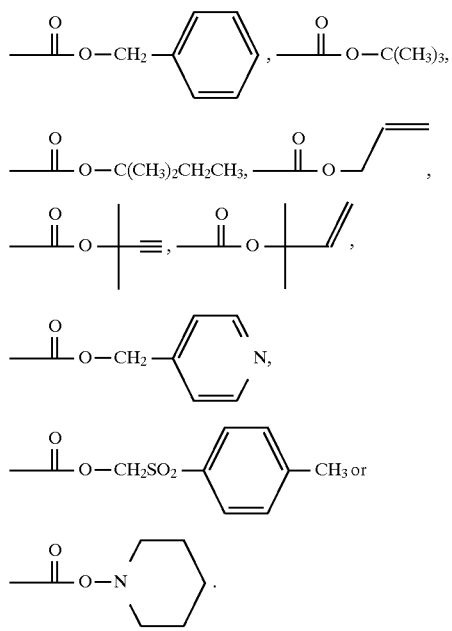

Particular interest also attaches to the process set out above in which latent pigments of the formula (IV) are used in which $L_1$ and $L_2$ independently of one another are $C_2$–$C_{18}$dialkylamino or $C_1$–$C_{18}$cycloalkylamino.

The latent pigments of the formulae (III) and (IV) are known substances whose synthesis is given, for example, in EP 648 770, EP 648 817, Angewandte Chemie 68/4, 133–150 (1956) or J. Org. Chem. 22, 127–132 (1957). Should some of them also be novel, they can be prepared in analogy to generally known methods. Instead of a latent pigment of the formula (IV) in which $L_1$ and $L_2$ are in positions 5/19, alternative possibilities are its positional isomers in which $L_1$ and $L_2$ are, for example, in positions 5/6, 5/13, 5/26, 5/28, 6/13 or 6/20, or a mixture of positional isomers. In many cases, it is not certain which positional isomer is produced in the abovementioned synthesis.

Preferred compounds of the formula (I) are i) 2,5-dihydropyrrolo[3,4-c]pyrroles of the formula

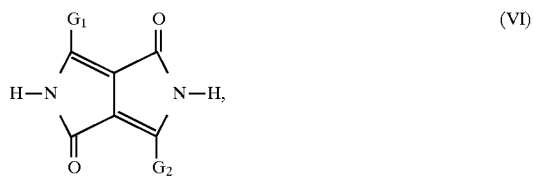 (VI)

in which $G_1$ and $G_2$ independently of one another are groups of the formula

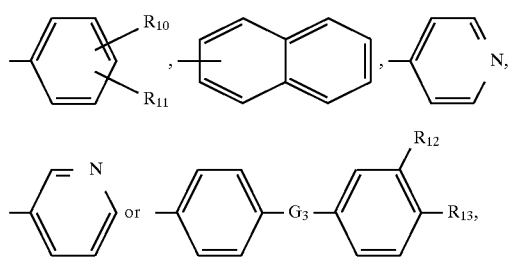

in which $G_3$ is —O—, —NR$_{14}$—, —N=N— or —SO$_2$—,
$R_{10}$ and $R_{11}$ independently of one another are hydrogen, chlorine, bromine, $C_1$–$C_4$alkyl, $C_1$–$C_6$alkoxy, $C_1$–$C_6$alkylamino, CN or phenyl,
$R_{12}$ and $R_{13}$ are hydrogen and
$R_{14}$ is hydrogen, methyl or ethyl;

ii) perylenecarboximides of the formula

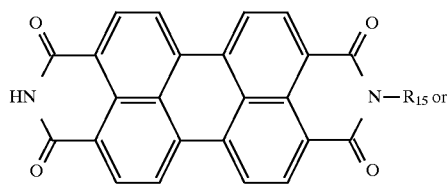

(VIIa)

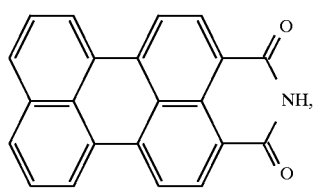

(VIIb)

in which $R_{15}$ is hydrogen, $C_1$–$C_6$alkyl, unsubstituted, halogen-substituted or $C_1$–$C_4$alkyl-substituted phenyl, benzyl or phenethyl;

iii) quinacridones of the formula

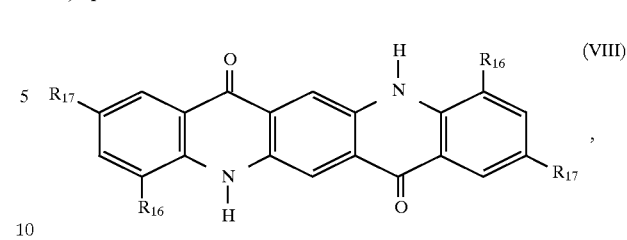

(VIII)

in which $R_{16}$ and $R_{17}$ independently of one another are hydrogen, halogen, $C_1$–$C_{18}$alkyl, $C_1$–$C_4$alkoxy or phenyl;

iv) dioxazines of the formula

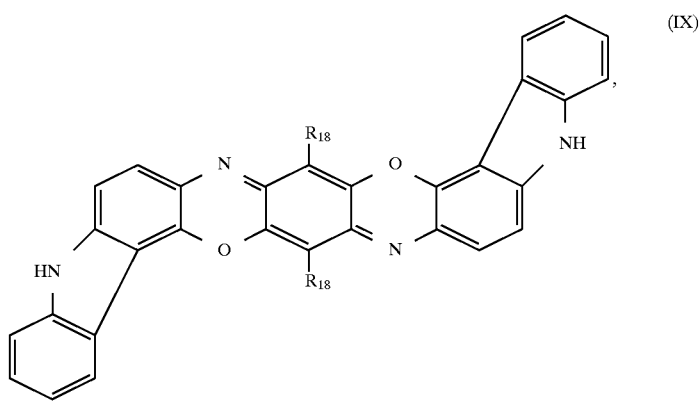

(IX)

in which $R_{18}$ is hydrogen, halogen or $C_1$–$C_{18}$alkyl;

v) isoindolines of the formulae

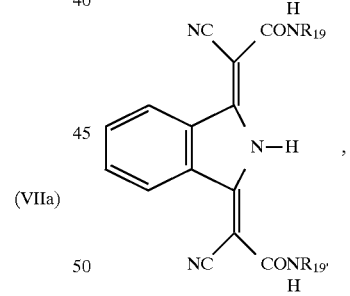

(Xa)

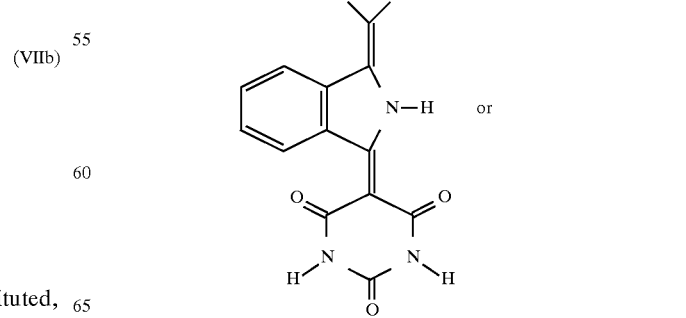

(Xb)

vi) derivatives of indigo, of the formula

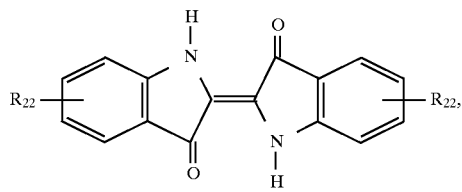

in which $R_{22}$ is hydrogen, CN, $C_1$–$C_4$alkyl, $C_1$–$C_4$alkoxy or halogen;

vii) benzimidazoloneazo compounds of the formula

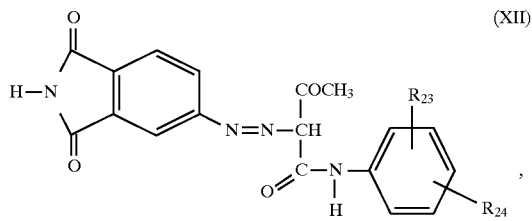

in which $R_{23}$ and $R_{24}$ independently of one another are hydrogen, halogen, $C_1$–$C_4$alkyl or $C_1$–$C_4$alkoxy;

viii) anthraquinonoid compounds of the formula

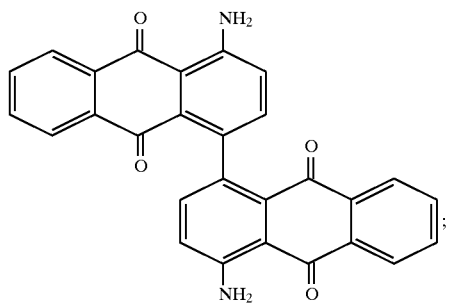

and ix) phthalocyanines of the formula

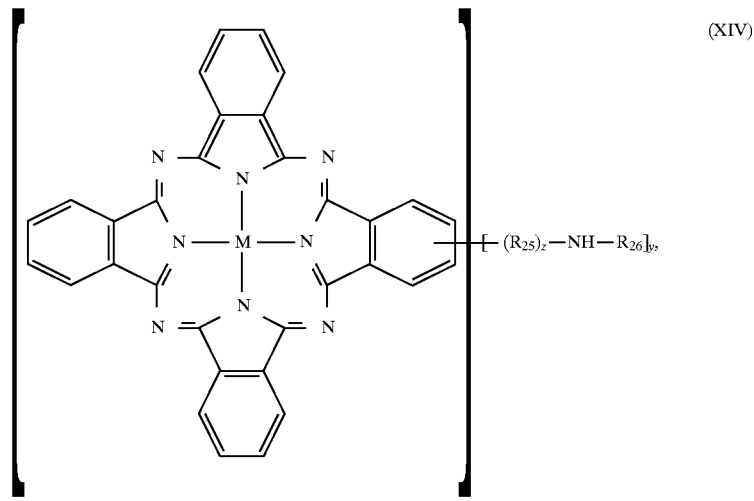

in which
M is $H_2$, Zn, Cu, Ni, Fe, TiO or VO,
$R_{25}$ is —CH($R_{27}$)— or —$SO_2$—,
$R_{26}$ is hydrogen, $C_1$–$C_4$alkyl, —NH$R_{27}$, —NHCOR$_{28}$, —COR$_{28}$ -continued

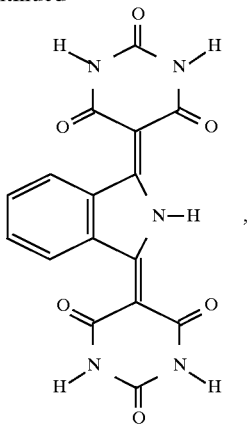

in which $R_{19}$ is hydrogen, $C_1$–$C_{18}$alkyl, benzyl or a group 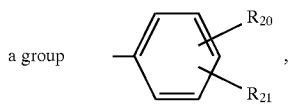, and $R_{19}'$ is a group 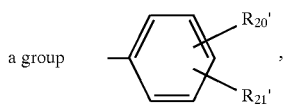, where $R_{20}$, $R_{21}$, $R_{20}'$ and $R_{21}'$ independently of one another are hydrogen, $C_1$–$C_{18}$alkyl, $C_1$–$C_4$alkoxy, halogen or trifluoromethyl;

or 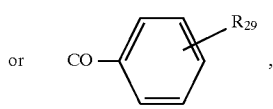, $R_{27}$ is hydrogen or $C_1$–$C_4$alkyl, $R_{28}$ is $C_1$–$C_4$alkyl, $R_{29}$ is hydrogen, halogen, $C_1$–$C_4$alkyl or $C_1$–$C_4$alkoxy, z is 0 or 1 and y is a number from 1 to 4.

Preferred compounds of the formula (II) are x) phthalocyanines of the formula

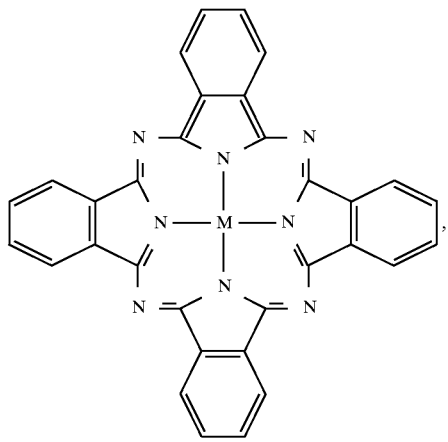 (XV)

in which

M is $H_2$, Zn, Cu, Ni, Fe, TiO or VO.

Particularly preferred pyrrolopyrroles are those of the formula (VI) in which $G_1$ and $G_2$ are identical, especially those in which $G_1$ and $G_2$ are identical groups of the formula

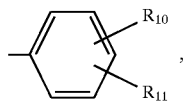, where $R_{10}$ and $R_{11}$ independently of one another are hydrogen, methyl, tert-butyl, chlorine, bromine, CN or phenyl, and very particularly those in which $R_{11}$ is hydrogen.

Among the phthalocyanines, particular preference is given to those of the formula (XIV) in which M is $H_2$, Cu or Zn, $R_{25}$ is —$CH_2$— or —$SO_2$—, $R_{26}$ is hydrogen, —$NHCOCH_3$ or benzoyl, $R_{27}$ is hydrogen and z is 1, and in particular to those of the formula (XV) in which M is $H_2$, Cu or Zn.

The substrate to be coated is not at all critical in terms of its chemical composition and its form. It may, for example, comprise metals, metal oxides, plastics, nonmetals or composite materials, such as glass, porcelain, bright, primed or coated steel, aluminium, silicon, indium/tin oxide, gallium arsenide, polyvinyl chloride, polyethylene terephthalate, polypropylene, polyamide, polyacrylate, polystyrene, and mixtures, alloys or copolymers thereof. These may comprise any goods and articles, for example in the form of plates, metal panels, films, tubes, fibres, woven fabrics, bottles, laminates or wafers.

Where the substrate material consists of or comprises a plastic, the latter may be any desired high molecular weight organic material, examples being vinyl polymers, such as polystyrene, poly-α-methylstyrene, poly-p-methylstyrene, poly-p-hydroxystyrene, poly-p-hydroxyphenylstyrene, poly(methyl acrylate) and poly(acrylamide) and the corresponding methacrylic compounds, poly(methyl maleate), poly(acrylonitrile), poly(methacrylonitrile), poly(vinyl chloride), poly(vinyl fluoride), poly(vinylidene chloride), poly(vinylidene fluoride), poly(vinyl acetate), poly(methyl vinyl ether) and poly(butyl vinyl ether); novolaks derived from $C_1$–$C_6$aldehydes, such as formaldehyde and acetaldehyde, and a bicyclic or preferably monocyclic phenol which is unsubstituted or substituted by one or two $C_1$–$C_9$alkyl groups, one or two halogen atoms or a phenyl ring, such as o-, m- or p-cresol, xylene, p-tert-butylphenol, p-chlorophenol or p-phenylphenol, o-, m- or p-nonylphenol, or a compound having more than one phenolic group, such as resorcinol, bis(4-hydroxyphenyl)methane or 2,2-bis(4-hydroxyphenyl)propane; polymers derived from maleimide and/or maleic anhydride, such as copolymers of maleic anhydride and styrene; poly(vinylpyrrolidone), biopolymers and their derivatives, such as cellulose, starch, chitin, chitosan, gelatine, zein, ethylcellulose, nitrocellulose, cellulose acetate and cellulose butyrate; natural resins and synthetic resins, such as rubber, casein, silicone and silicone resins, ABS, urea- and melamine-formaldehyde resins, alkyd resins, phenolic resins, polyamides, polyimides, polyamide/imides, polysulfones, polyether sulfones, polyphenylene oxides, polyurethanes, polyureas, polycarbonates, polyarylenes, polyarylene sulfides, polyepoxides, polyolefins and polyalkadienes.

Preferred high molecular weight organic materials are cellulose ethers and cellulose esters, such as ethylcellulose, nitrocellulose, cellulose acetate or cellulose butyrate, natural resins or synthetic resins, such as addition polymerization or condensation resins, such as amino resins, especially urea- and melamine-formaldehyde resins, alkyd resins, phenolic resins, polycarbonates, polyesters, polyolefins, polystyrene, polyvinyl chloride, polyamides, polyurethanes, ABS, polyphenylene oxides, silicone and silicone resins, and mixtures thereof.

For the coating operation, a latent pigment is simply melted or, preferably, dissolved in an appropriate solvent. Mixtures of latent pigments can also be used, the individual components being melted together or in succession or dissolved in an appropriate solvent whereby relatively low mixed melting points or relatively high concentrations are possible. The latent pigment is preferably dissolved with stirring at a somewhat elevated temperature, expediently between 30° C. and the boiling point of the solvent.

Appropriate solvents are all customary solvents such as, inter alia, hydrocarbons, alcohols, amides, nitriles, nitro compounds, N heterocycles, ethers, ketones and esters, which may if desired also be mono- or polyunsaturated or chlorinated, examples being methanol, ethanol, isopropanol, diethyl ether, acetone, methyl ethyl ketone, 1,2-dimethoxyethane, 1,2-diethoxyethane, 2-methoxyethanol, ethyl acetate, tetrahydrofuran, dioxane, acetonitrile, benzonitrile, nitrobenzene, N,N-dimethylformamide, N,N-dimethylacetamide, dimethyl sulfoxide, N-methylpyrrolidone, pyridine, picoline, quinoline, trichloroethane, benzene, toluene, xylene, anisole and chlorobenzene. Further examples of solvents are described in numerous table collations and reference works. In place of a single solvent, it is also possible to employ mixtures of two or more solvents.

Preference is given to those solvents which dissolve the substrate to be coated either not at all or only very slowly, and which have a boiling point between 40° C. and 170° C., especially aromatic hydrocarbons, alcohols, ethers, ketones and esters. Particular preference is given to toluene, methanol, ethanol, isopropanol, 1,2-dimethoxyethane, 1,2-diethoxyethane, acetone, methyl ethyl ketone, ethyl acetate, tetrahydrofuran and dioxane, and to mixtures thereof.

The preferred concentration of the latent pigments in a solvent is approximately 80–99% of the saturation concentration, with the use of supersaturated solutions being possible as well in some cases without premature precipitation of the solvate. For many latent pigments of the formulae (III) and (IV), the optimum concentration is ~0.1–50% by weight, often 1–20% by weight.

The choice of the solvent and of the optimum concentration should take into account the requirements of the chosen coating technology with regard to the physical properties of the solution, such as for example the density, the vapour pressure and, in particular, the viscosity.

Where the solution contains undissolved particles, for example dust, pigment particles or other impurities, or where complicated coating techniques are used, for example spin coating, it is advisable to filter this solution prior to its further use, a filter with very fine pores being used with particular advantage. A dust-free environment, for example a clean air room, is also advisable.

Coating can be carried out by any desired known technique, such as by dipping, spraying, printing, curtain coating, knife coating or spin coating. Such customary techniques and their advantages and disadvantages are described very well in a large number of publications. Particularly advantageous and homogeneous coatings are obtained by spin coating.

In the course of coating, the substrate can be coated overall or, preferably, over only part of its surface, to form coloured patterns. Some coating techniques lead automatically to patterns, such as in the case of printing where the pattern follows that of the printing plate, while with other coating techniques it is possible to use customary patterning aids, such as a stencil when spraying. It is preferred for the substrate in step (a) of the process according to the invention to be coated over only part of its surface.

After the coating operation, it is expedient to remove part or all of the solvent by evaporating it at, for example, from 0.1 to 1.0 bar. The solvent is preferably evaporated under an exhaust hood to a residual quantity of $\leq 50\%$ by weight, based on the latent pigment, at a temperature of 1°–50° C. below the flash point of the solvent and at a pressure of 0.7–1.0 bar.

The latent pigment applied as a coating to the substrate is then converted partially or completely into its insoluble pigment form. In this cases it is necessary to remove the group $D_3$ and, if appropriate, $D_4$ in formula (III) or, respectively, $L_1$ and $L_2$ in formula (IV). In the case of latent pigments of the formula (III) this step takes place with ease, the groups $D_3$ and, if appropriate, $D_4$ fragmenting and being replaced on the chromophore radical by hydrogen atoms. In the case of latent pigments of the formula (IV) this step likewise takes place with ease, although $L_1$ and $L_2$ do not leave behind any hydrogen atoms (in other words, formal elimination takes place).

The conversion (b) of the latent pigments into their insoluble form can be carried out very easily by, alternatively, thermal treatment (heating at temperatures for example between 50° and 400° C., preferably at from 100° to 200° C., especially by the close action of a heat source or by irradiation with infrared light), photolytic treatment (irradiation, for example, with UV light of wavelength $\leq 375$ nm) or chemical treatment (exposure to the vapour of an organic or inorganic Bronsted or Lewis acid or of a base, such as hydrochloric acid, trifluoroacetic acid, boron trifluoride, ammonia or 4-dimethylaminopyridine). The conversion methods mentioned can also be combined, as for example in the case of irradiation with an unfocused or, particularly preferably, with a focused laser beam, for example the beam from an argon ion laser with lines at 488 and 514 nm, from a $CO_2$ laser with lines at ~10 μm or from an Nd:YAG laser with its principal line at 1064 nm, with or without frequency doubling.

By the choice of conditions for converting (b) the latent pigments into their insoluble form, it is possible reproducibly to influence the structure of the pigment coating, especially in respect of the pigment particle size. For example, under different conditions it is possible to obtain alternatively fine (diameter $\leq 0.1$ μm), medium (diameter ~0.1–1 μm) or else coarse (diameter $\geq 1$ μm) pigment particles. In many cases it has been found favourable to heat the substrate itself, during conversion, to a slightly elevated temperature (~50°–80° C.).

In step (b) of the process according to the invention, the latent pigment can be converted, quantitatively and over the full area, into its insoluble pigment form. Preferably, however, step (b) takes place only at selected areas, it being possible very easily to obtain structured colour patterns. The resolut on of such structures depends on the dimension of the means used for the conversion, i.e. for ex ample on the dimensions of a thermocouple used as heat source or on the diameter of a focused or unfocused light beam used as the means of irradiation.

If a laser beam is used for selective conversion, then structured colour patterns with particularly high resolutions in the case of the structured colour patterns obtained are possible, for example from 1 μm to 1 mm, preferably 5–200 μm, particularly preferably 10–50 μm. Resolution in this context is understood to be the minimum possible interval between two successive lines which are separated by empty lines. Using laser beams and thermocouples it is possible to obtain structured colour patterns in a simple and rapid manner, for example with a laser marking device or in analogy to the known technologies of laser printers or thermal printers. Such operations are preferably directed using programmed control, particularly preferably with full automation, expediently witha memory-programmed control or with a computer with fixed or variable data. The choice of structured colour patterns is arbitrary; it may compr ise successive pixels, arranged for example in a spiral, bar codes, letters or text strokes, and geometrical or artistically designed forms, for example brand symbols.

Where no high resolution is required, for decorative purposes for example, it is also possible to adopt a procedure in which the coloured pattern produced as described above in step (a) is converted in step (b) over the entire area into the insoluble pigment form. It is also possible, however, to produce in step (a) the general outline of the coloured pattern desired, and then in step (b) to convert the desired coloured pattern with high resolution into the insoluble pigment form. Likewise, well-resolved structures can also be produced by carrying out irradiation through a fixed or programmable mask, for example through a stencil or a liquid-crystal screen.

Where step (b) is carried out only at selected areas, it leaves not only the areas with the pigment coating but also areas containing unchanged latent pigment. If the conditions under which the latent pigment is converted into the insoluble pigment form are mild in comparison with the stability of the latent pigment, then sometimes it is also possible to carry out only partial conversion of some of the latent pigment, so that the pigment coating still contains soluble portions. In both cases, steps (a) and (b) are preferably followed by additional step (c) comprising the removal of the remaining latent pigment.

The remaining latent pigment is preferably removed with the aid of a solvent, for example by dipping, in countercurrent for example, or by rinsing, for example with a pressure syringe or in condensing steam, with or without a mechanical aid such as brushing, agitation or ultrasound. Preference is given to the same solvents as for the coating operation. The solution of the remaining latent pigment recovered can be recycled directly or after cleaning, for example by filtration.

After a pigment coating has been applied to a substrate by the process according to the invention, it is possible to apply another pigment coating in the same way, so that the substrate has two or more pigment coatings. This procedure can, in principle, be repeated as often as is desired.

The invention therefore also provides a process in which two or more pigment coatings are applied to the substrate surface by successive application of these pigment coatings, repeating steps (a) to (c) for each pigment coating.

The method according to the invention surprisingly renders possible very homogeneous, uniform and transparent coatings of high stability. At the outer edge of a colour pattern there is a narrow zone whose width depends on the resolution of the conversion method and on the thermal conductivity of the substrate, and is for example $\leq 5–10\,\mu m$ with a well-focused laser. The uniformity of the thickness of the pigment coating corresponds to that of the latent pigment; depending on the coating method it varies by less than $\pm 25\%$, usually less than $\pm 10\%$, and in the case of precision coating techniques such as centrifugation the variation drops even to below $\pm 1\%$. Qualitatively, the reflection spectrum is of equal opacity at all points; quantitatively, it depends only on the coating thickness.

Apart from this, the pigment coating is substantially uniform at the areas where the latent pigment has been converted into its insoluble pigment form. It is possible, in particular, to obtain very uniformly distributed, fine pigment particles (with a diameter of, for example, $\leq 0.1\,\mu m$), resulting in outstandingly transparent and bright colorations. The pigment coating is entirely absent from the areas where there is no treatment to convert the latent pigment into its insoluble pigment form, and consequently the optical transparency of these areas corresponds to that of the bare substrate.

The invention therefore also provides a material comprising a substrate whose surface carries at least one pigment coating consisting of one or more pigments of the formula (I) or (II) according to claim 1, which coating is substantially uniform on one part of the substrate surface and is absent from the remainder of the substrate surface.

For protection against external influences it is possible additionally to provide the material according to the invention with a protective coat, for example with a coating material consisting of one of the abovementioned plastics and also containing, if desired, additives to improve the pigment properties further, examples being light stabilizers such as hindered amines, or UV absorbers, such as hydroxybenzophenones, hydroxyphenylbenzotriazoles, hydroxyphenyltriazines or oxalanilides. In the case of two or more pigment coatings it is also possible to provide a protective coat between the individual coatings, so that the subsequent pigment coating is applied not directly to the substrate but instead to this intermediate coat.

The material according to the invention can have one or more pigment coatings. Where two or more pigment coatings are applied to a substrate, then preference is given to coatings comprising pigments of the formula (I) or (II) or mixtures thereof which have different absorptions, such as a broad or sharp absorption band, or different absorption maxima, such as 450 nm and/or 550 nm or 650 nm. In this case, each of the pigment coatings preferably forms an independent pattern whose coverage is not identical to that of the patterns of the other pigment coatings, with the result that multicoloured patterns are produced. The invention consequently also provides a material in which the substrate is coated with a plurality of pigment coatings which do not form patterns of equal coverage and have different absorptions and/or different absorption maxima.

Particular preference is given to a material of this kind in which the pigment coatings consist of pigments whose nature and arrangement is such as to give blue, green and red areas, and in which the substrate is transparent.

Instead of a plurality of different-coloured pigment coatings it is also possible to have a plurality of pigment coatings of different thicknesses, containing identical or identically coloured pigments. Where these coats overlap, then, depending on the nature of the overlapping, patterns of different colour intensities are produced. The total absorption, which is given by the sum of the intensities of all overlapping pigment coatings, at each pixel which has at least one pigment coating is preferably a multiple of the value of the smallest absorption. The smallest absorption is that of the thinnest pigment coating and occurs at pixels where this thinnest coating does not overlap with any other pigment coating. Advantageous pigment coatings are those whose relative coat thickness (or whose relative absorptions) are in a ratio 1, 2, 4, 8 . . . $2^n$, whereby the intermediate values are also possible by controlled overlapping. Different coat thicknesses can also be combined with different-coloured pigment coatings.

The materials according to the invention can be used for decorative coloration. Preference, however, is given to their use for the permanent storage of digital information, and particular preference to their use as colour filters, an application which is particularly suitable for the already mentioned materials which consist of a transparent substrate and of areas having blue, green and red pigment coatings. Where the materials are used as colour filters, or for storing digital information, particular advantages are the high resolution, the high transparency, the excellent pigment stability in comparison with corresponding soluble dyes, and the substantially thinner coats relative to mass coloration.

Where the material according to the invention is used to store digital information, this information can be recorded by irradiating the material with a light source, for example with a focused laser beam, and read by measuring the intensity of the reflected or transmitted light beam, which is preferably of substantially lower energy. The homogeneity and stability of the pigment coating enables frequent, precise reading operations to be carried out with no reduction in reading quality. Materials having a plurality of identical, overlapping pigment coatings of different thickness produce signals of different intensities, so that a plurality of bits can be stored per pixel. The invention, consequently, additionally provides a method out reading of digital information stored on a material according to the invention by irradiation with a light source and measurement of the intensity of the reflected or transmitted light beam.

The examples which follow illustrate the invention:

EXAMPLE 1

A solution of 100 mg N,N'-bis(tert-butoxycarbonyl)-3,6-diphenyl-1,4-diketo-pyrrolo-[3,4-c]pyrrole of the formula (XVIa)

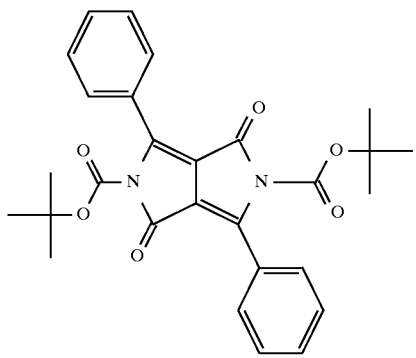
(XVIa)

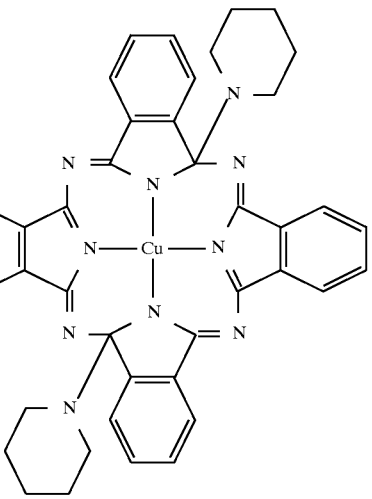
(XVIIa)

(XVIb)

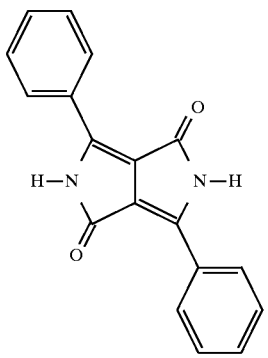

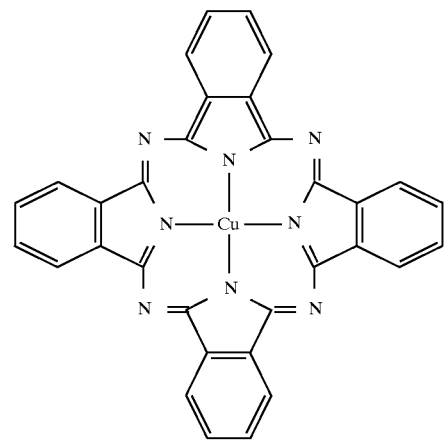
(XVIIb)

in 2 ml of dioxane is spin-coated at 1000 rpm onto a 38×26×1 mm glass support. The resulting coat is dried at 90° C. for 1 minute. The yellow coat has a thickness of ~360 nm, and the optical density at $\lambda_{max}$=430 nm is 0.90. The coated support is then heated for 5 minutes on a plate which has been preheated to 200° C., whereupon the colour changes to the characteristic red colour of 2,5-dihydro-3,6-diphenyl-1,4-diketopyrrolo[3,4-c]pyrrole of the formula (XVIb). The resulting coat has a thickness of ~250 nm, and the optical density at $\lambda_{max}$=540 nm is 0.80. The absorption spectrum obtained after thermal treatment is identical with that of 2,5-dihydro-3,6-diphenyl-1,4-diketopyrrolo[3,4-c]pyrrole. The coat exhibits outstanding transparency and homogeneity.

EXAMPLE 2

A solution of 100 mg leucophthalocyanine of formula (XVIIa)

in 2 ml of dioxane is spin-coated at 1000 rpm onto a 38×26×1 mm glass support. The resulting coat is dried at 90° C. for 1 minute. The pale yellowish coat has a thickness of ~320 nm, and the optical density at $\lambda_{max}$=311 nm is 1.05. The coated support is then heated for 5 minutes on a plate which has been preheated to 200° C., whereupon the colour changes to the characteristic blue colour of copper phthalocyanine of the formula (XVIIb). The resulting coat has a thickness of ~300 nm, and the optical density at $\lambda_{max}$=620 nm is 0.87. The absorption spectrum obtained after thermal treatment is identical with that of copper phthalocyanine. The coat exhibits outstanding transparency and homogeneity.

EXAMPLE 3

A solution of 100 mg N,N'-bis(tert-butoxycarbonyl)-3,6-diphenyl-1,4-diketopyrrolo[3,4-c]pyrrole of the formula (XVIa) in 2 ml of dioxane is spin-coated at 1000 rpm onto a 38×26×1 mm glass support. The resulting coat is dried at 90° C. for 2 minutes. The yellow coat has a thickness of ~360 nm, and the optical density at $\lambda_{max}$=430 nm is 0.90. The coated support is then stored for 30 minutes at 25° C. in hydrogen chloride vapour, whereupon the colour changes to the characteristic red colour of 2,5-dihydro-3,6-diphenyl-1,4-diketopyrrolo[3,4-c]pyrrole of the formula (XVIb). The resulting coat has a thickness of ~250 nm, and the optical density at $\lambda_{max}$=540 nm is 0.80. The absorption spectrum obtained after acid treatment is identical with that of 2,5-dihydro-3,6-diphenyl-14-diketopyrrolo[3,4-c]pyrrole. The coat exhibits outstanding transparency and homogeneity.

EXAMPLE 4

A solution of 100 mg dioxazine derivative of formula (XVIIIa)

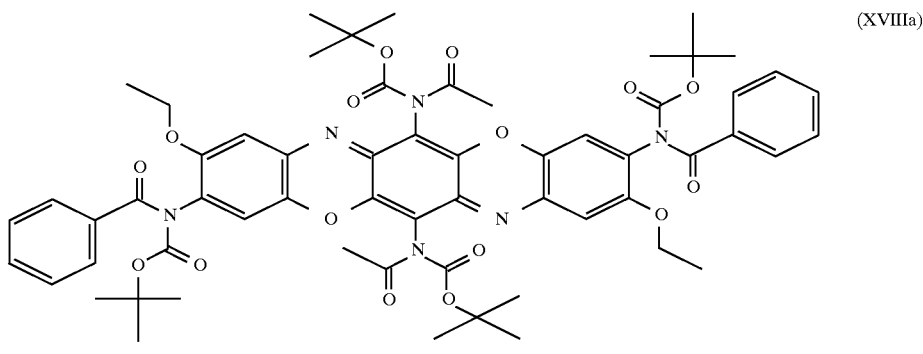

(XVIIIa)

in 2 ml of dioxane is spin-coated at 1000 rpm onto a 38×26×1 mm glass support. The resulting coat is dried at 90° C. for 1 minute. The red coat has a thickness of ~120 nm, and the optical density at $\lambda_{max}$=561 nm is 0.56. The coated support is then heated for 5 minutes on a plate which has been preheated to 200° C., whereupon the colour changes to the characteristic violet colour of the dioxazine pigment of the formula (XVIIIb=C.I. Pigment Violet 37).

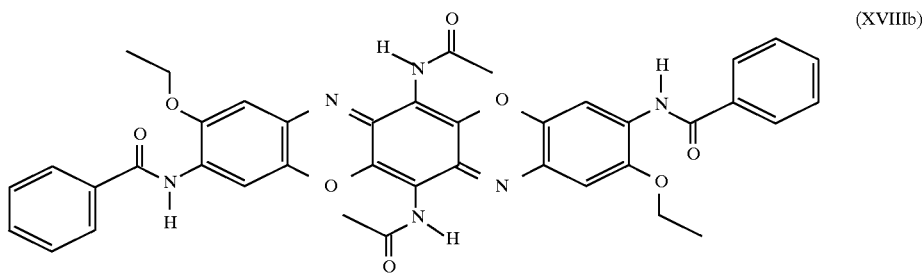

(XVIIIb)

The resulting coat has a thickness of ~80 nm, and the optical density at $\lambda_{max}$=553 nm is 0.43. The absorption spectrum obtained after thermal treatment is identical with that of C.I. Pigment Violet 37. The coat exhibits outstanding transparency and homogeneity.

EXAMPLE 5

A solution of 100 mg of the compound of the formula (XVIIIa) in 2 ml of dioxane is spin-coated at 1000 rpm onto a 38×26×1 mm glass support. The resulting coat is dried at 90° C. for 1 minute. The yellow coat has a thickness of 120 nm, and the optical density at $\lambda_{max}$=561 nm is 0.56. The coated support is then exposed using the focused beam of an Ar ion laser (visible, all lines; primarily 488 and 514 nm). In this operation, the laser beam is guided over the coat by way of a movable mirror (laser marking apparatus) at a predetermined speed under computer control. At a laser output of 1.5 W, with the writing speed set at between 75 and 400 mm/s, the marked areas undergo a colour change to the characteristic violet colour of the dioxazine pigment of the formula (XVIIIb=C.I. Pigment Violet 37). The support is subsequently washed with 20 ml diethyl ether, with only the marked (insoluble) structures remaining in relief on the glass support. The resolution is $\leq$50 μm.

EXAMPLE 6

The procedure of Example 5 is repeated, but using a 50×75×2 mm sheet of polycarbonate ®Makrolon, Bayer) as support and marking at an output of 1.0 W. The results are comparable with those of Example 5.

EXAMPLE 7

The procedure of Example 1 is repeated, but carrying out exposure with the focused beam of an Ar ion laser with UV mirror (UV, all lines; primarily 351 and 364 nm) at an output of 0.4 W. The results are comparable with those of Example 5.

EXAMPLE 8

As in Example 1, a solution of 100 mg N,N'-bis(tert-butoxycarbonyl)-3,6-diphenyl-1,4-diketopyrrolo[3,4-c] pyrrole of the formula (XVIa) in 2 ml of dioxane is spin-coated at 1000 rpm onto a 38×26×1 mm glass support. The resulting coat is dried at 90° C. for 1 minute. The yellow coat has a thickness of ~360 nm, and the optical density at $\lambda_{max}$=430 nm is 0.90. The coated support is then exposed using the focused beam of an Ar ion laser (visible, all lines; primarily 488 and 514 nm). At a laser output of 2.5 W, with a writing speed set at 75 mm/s, the marked areas undergo a colour change to the characteristic red colour of the diketopyrrolopyrrole pigment of the formula (XVIb).

EXAMPLE 9

The procedure of Example 8 is repeated, but carrying out exposure with the focused beam of an Ar ion laser with UV mirror (UV, all lines; primarily 351 and 364 nm) at an output of 0.8 W and a writing speed of 5 mm/s. The results are comparable with those of Example 8.

EXAMPLE 10

As in Example 2, a solution of 100 mg leucophthalocyanine of the formula (XVIIa) in 2 ml of dioxane is spin-coated at 1000 rpm onto a 38×26×1 mm glass support. The resulting coat is dried at 90° C. for 1 minute. The pale yellowish coat has a thickness of ~320 nm, and the optical density at $\lambda_{max}$=311 nm is 1.05. The coated support is then exposed using the focused beam of an Ar ion laser (visible, all lines; primarily 488 and 514 nm). At a laser output of 2.5 W and a writing speed of between 75 and 200 mm/s, the marked areas undergo a colour change to the characteristic blue colour of the phthalocyanine pigment of the formula (XVIIb).

EXAMPLE 11

The procedure of Example 10 is repeated, but carrying out exposure with the focused beam of an Ar ion laser with UV mirror (UV, all lines; primarily 351 and 364 nm) at an output of 0.8 W and a writing speed of between 5 and 60 mm/s. The results are comparable with those of Example 10.

EXAMPLE 12

The procedure of Example 10 is repeated, but using, instead of the product of the formula (XVIIa), N,N'-bis(neopentoxycarbonyl)dioxazine of the formula (XIXa)

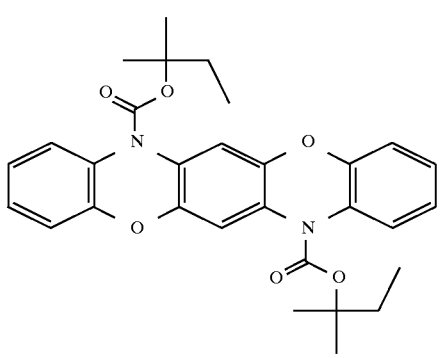

which was prepared by the method indicated in EP 648 817. The coated support is then exposed using the focused beam of an Ar ion laser (visible, all lines; primarily 488 and 514 nm). At a laser output of 2.5 W and a writing speed of between 75 and 200 mm/s, the marked areas undergo a colour change to the characteristic violet colour of the dioxazine pigment of the formula (XIXb):

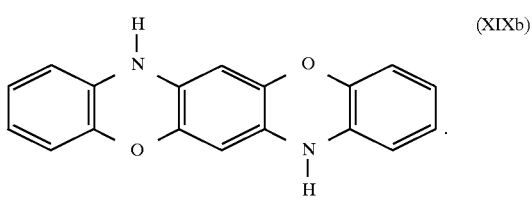

The support is subsequently washed with 20 ml of diethyl ether, to leave only the marked (insoluble) structures in relief on the glass support. The resolution is $\leq 50 \mu m$.

What is claimed is:

1. A process for the preparation of a material comprising a substrate on the surface of which there is at least one pigment coating consisting of one or more pigments of the formula (I)

$$A(D_1)(D_2)_x \qquad (I)$$

in which A is the radical of an unsubstituted or mono- or polysubstituted chromophore of the quinacridone, anthraquinone, perylene, indigo, azo, quinophthalone, isoindolinone, isoindoline, dioxazine, phthalocyanine or diketopyrrolopyrrole series which contains nitrogen atoms attached to $D_1$ and to x $D_2$, each nitrogen atom present in A being able independently of the others to be attached to 0, 1 or 2 groups $D_1$ or $D_2$, $D_1$ and $D_2$ are hydrogen, and x is an integer from 0 to 4, which pigment coating is applied by (a) coating at least a portion of the substrate surface with a melt of at least one unsubstituted or mono- or polysubstituted latent pigment of the formula (III), or a solution consisting essentially of at least one latent pigment of formula (III) and one or more solvents, $$A(D_3)(D_4)_x \qquad (III)$$

A and x in formula (III) having the same meaning as in formula (I), A containing nitrogen atoms attached to $D_3$ and to x $D_4$, and each nitrogen atom present in A being able independently of the others to be attached to 0,1 or 2 groups $D_3$ or $D_4$, and $D_3$ and $D_4$ independently of one another being groups of the formula

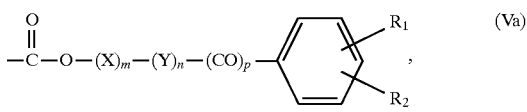

(b) converting at least a portion of the latent pigment into its insoluble pigment form by eliminating groups $D_3$ and $D_4$ and replacing the eliminated groups with hydrogen, and (c) removing any remaining latent pigment from the surface of said material, where, in the formulae (Va), (Vb) and (Vc), m, n and p independently of one another are 0 or 1, X is $C_1$–$C_{14}$alkylene, $C_2$–$C_{14}$alkenylene, $C_2$–$C_4$alkynylene, $C4$–$C1_2$cycloalkylene or $C_4$–$C_{12}$cycloalkenylene, Y is a group —V—$(CH_2)_q$—;

Z is a group —V—$(CH_2)_r$—,

V is $C_3$–$C_6$cycloalkylene, q is a number from 1 to 6, r is a number from 0 to 6, $R_1$ and $R_2$ independently of one another are hydrogen, $C_1$–$C_6$alkyl, $C_1$–$C_4$alkoxy, halogen, CN, $NO_2$, phenyl which is unsubstituted or substituted by $C_1$–$C_4$alkyl, $C_1$–$C_4$alkoxy or halogen, or are phenoxy, Q is hydrogen, CN, $Si(R_1)_3$, a group $C(R_5)(R_6)(R_7)$, in which $R_5$, $R_6$ and $R_7$ independently of one another are hydrogen or halogen and at least one of the radicals $R_5$, $R_6$ and $R_7$ is halogen, a group $SO_2$— 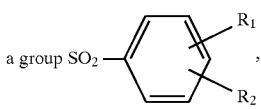, in which $R_1$ and $R_2$ are as defined above,
a group $SO_2R_8$ or $SR_8$, in which $R_8$ is $C_1$–$C_4$alkyl,
a group $CH(R_9)_2$, in which $R_9$ is phenyl which is unsubstituted or substituted by $C_1$–$C_4$alkyl, $C_1$–$C_4$alkoxy or halogen,
or a group of the formula

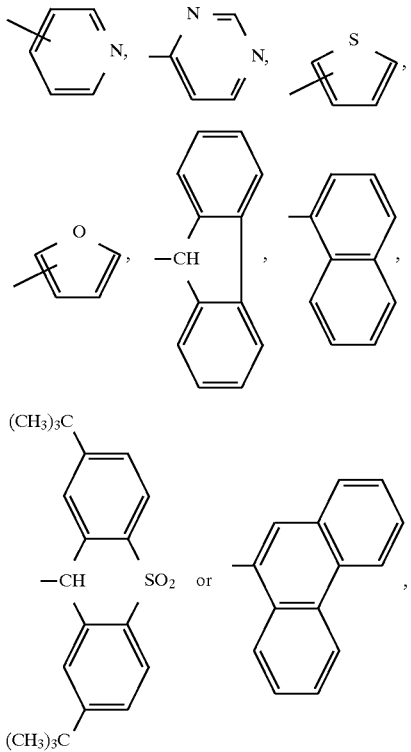

and
$R_3$ and $R_4$ independently of one another are hydrogen, $C_1$–$C_{18}$alkyl, or a group —(X)$_m$—(Y)$_n$— 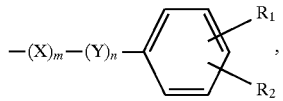, in which X, Y, $R_1$, $R_2$, m and n are as defined above, or $R_3$ and $R_4$ together with the nitrogen atom to which they are attached form a pyrrolidinyl, piperidyl or morpholinyl radical.

2. A process according to claim 1, wherein the substrate is coated in step (a) over only part of its surface.

3. A process according to claim 1, wherein step (a) is effected by dipping, spraying, printing, curtain coating, knife coating or spin coating.

4. A process according to claim 3, wherein step (a) is effected by spin coating.

5. A process according to claim 1, wherein step (b) is effected by means of a focused laser beam.

6. A process according to claim 1, wherein step (b) is effected by the close action of a heat source.

7. A process according to claim 1, wherein step (b) is effected by exposure to the vapour of an organic or inorganic Bronsted or Lewis acid or of a base.

8. A process according to claim 1, wherein step (b) is effected only at selected areas.

9. A process according to claim 8, wherein step (b) is effected with a programmed control.

10. A process according to claim 1, wherein step (c) is effected with the aid of a solvent.

11. A process according to claim 1, wherein two or more pigment coatings are applied to the substrate surface by successive application of these pigment coatings, repeating steps (a) to (c) for each pigment coating.

12. A material comprising a substrate whose surface carries at least one pigment coating consisting of one or more pigments of the formula (I) according to claim 1, which coating is substantially uniform on a part of the substrate surface and is absent from the remainder of the substrate surface.

13. A material according to claim 12, wherein at least one pigment coating has structured colour patterns with a resolution of 10–50 μm.

14. A material according to claim 12, which is additionally provided with a protective coat.

15. A material according to claim 12, wherein the substrate is coated with a plurality of pigment coatings which do not form patterns of equal coverage and have different absorptions and/or different absorption maxima.

16. A material according to claim 15, wherein the pigment coatings consist of pigments whose nature and arrangement is such as to give blue, green and red areas and wherein the substrate is transparent.

17. A material according to claim 12, wherein a plurality of pigment coatings of different thicknesses, containing identical or identically coloured pigments, form patterns, so that the total absorption, which is given by the sum of the intensities of all overlapping pigment coatings, at each pixel which has at least one pigment coating is a multiple of the value of the smallest absorption.

18. A material according to claim 12 which is a color filter.

19. A material according to claim 12 which is a means for the permanent storage of digital information.

20. A method of reading out digital information stored on a material according to claim 12 by irradiation with alight source and measurement of the intensity of the reflected or transmitted light beam.

21. A process of claim 1, wherein in formula $$A(D_3)(D_4)_x \quad (III)$$

x is 0 or 1 and $D_3$ and $D_4$ independently of one another are groups of the formula

 (Va)

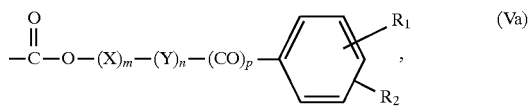

 (Vb)

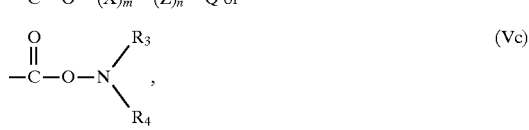 (Vc)

n and p are both 0,
m is 0 or 1,

Q is hydrogen, CN, CCl$_3$,

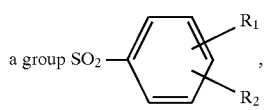

SO$_2$CH$_3$ or SCH$_3$,

X is C$_1$–C$_4$alkylene or C$_2$–C$_5$alkenylene,

R$_1$ and R$_2$ independently of one another are hydrogen, C$_1$–C$_4$alkyl, methoxy, chlorine or NO$_2$, and R$_3$ and R$_4$ independently of one another are hydrogen, C$_1$–C$_4$alkyl or a group

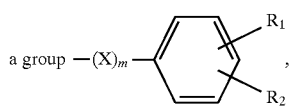

or R$_3$ and R$_4$ together form a piperidyl radical.

22. A process of claim 21, wherein in formula (III) x is 1 and D$_3$ and D$_4$ are identical and are groups of the formula

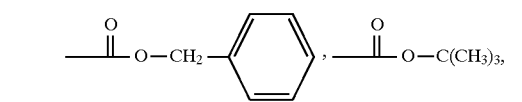

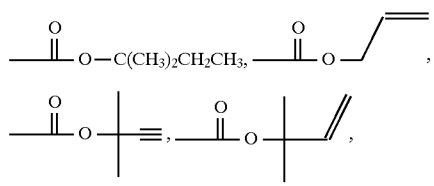

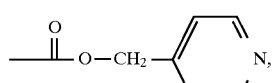

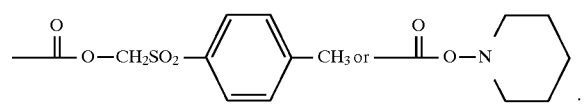

23. A process of claim 1, wherein the pigment of formula (I) is selected from the group consisting of i) 2,5-dihydropyrrolo[3,4-c]pyrroles of the formula

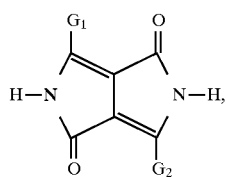
(VI)

in which G$_1$ and G$_2$ independently of one another are groups of the formula

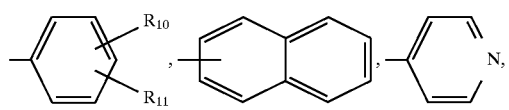

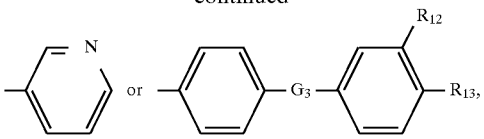

in which G$_3$ is —O—, —NR$_{14}$—, —N=N— or —SO$_2$—,

R$_{10}$ and R$_{11}$ independently of one another are hydrogen, chlorine, bromine, C$_1$–C$_4$alkyl, C$_1$–C6alkoxy, C$_1$–C$_6$alkylamino, CN or phenyl, R$_{12}$ and R$_{13}$ are hydrogen and R$_{14}$ is hydrogen, methyl or ethyl;

ii) perylenecarboximides of the formula

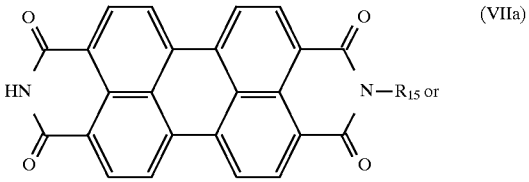
(VIIa)

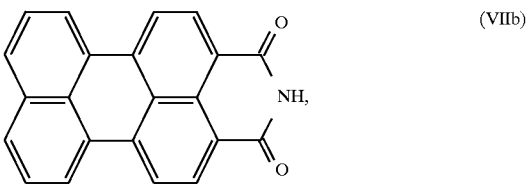
(VIIb)

in which R$_{15}$ is hydrogen, C$_1$–C$_6$alkyl, unsubstituted, halogen-substituted or C$_1$–C$_4$alkyl-substituted phenyl, benzyl or phenethyl;

iii) quinacridones of the formula

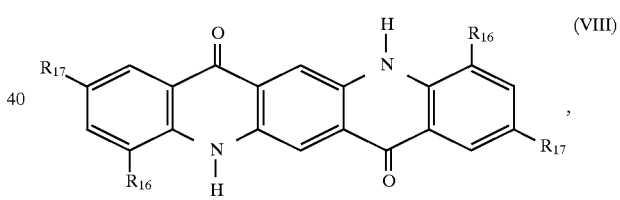
(VIII)

in which R$_{16}$ and R$_{17}$ independently of one another are hydrogen, halogen, C$_1$–C$_8$alkyl, C$_1$–C$_4$alkoxy or phenyl;

iv) dioxazines of the formula

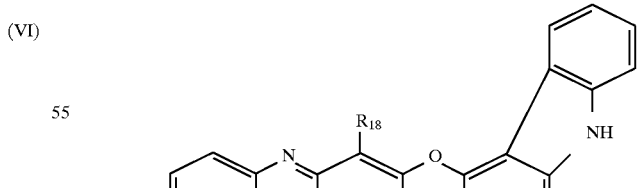
(IX)

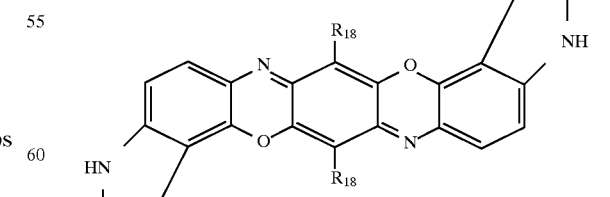

in which R$_{18}$ is hydrogen, halogen or C$_1$–C$_{18}$alkyl;

v) isoindolines of the formulae

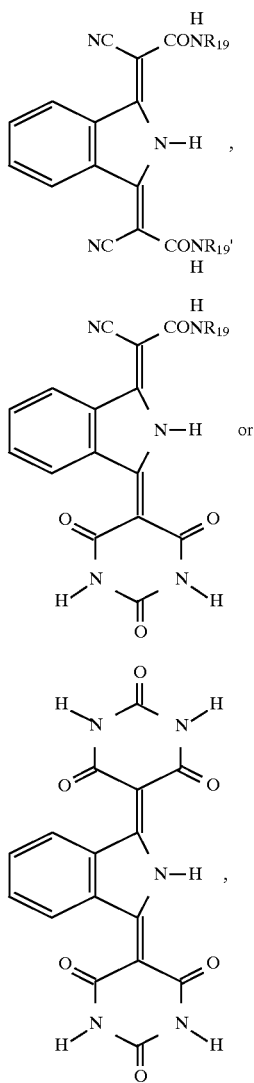

in which $R_{19}$ is hydrogen, $C_1-C_{18}$alkyl, benzyl or

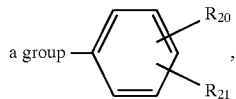

and $R_{19}'$ is

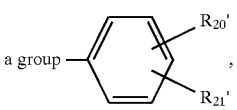

where $R_{20}$, $R_{21}$, $R_{20}'$ and $R_{21}'$ independently of one another are hydrogen, $C_1-C_{18}$alkyl, $C_1-C_4$alkoxy, halogen or trifluoromethyl;

vi) derivatives of indigo, of the formula

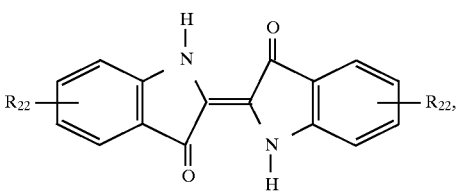

in which $R_{22}$ is hydrogen, CN, $C_1-C_4$alkyl, $C_1-C_4$alkoxy or halogen;

vii) benzimidazoloneazo compounds of the formula

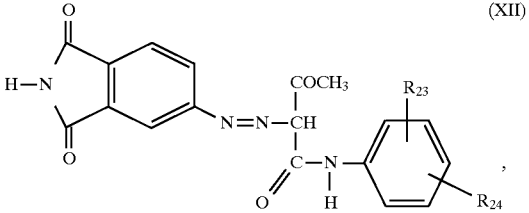

in which $R_{23}$ and $R_{24}$ independently of one another are hydrogen, halogen, $C_1-C_4$alkyl or $C_1-C_4$alkoxy;

viii) anthraquinonoid compounds of the formula

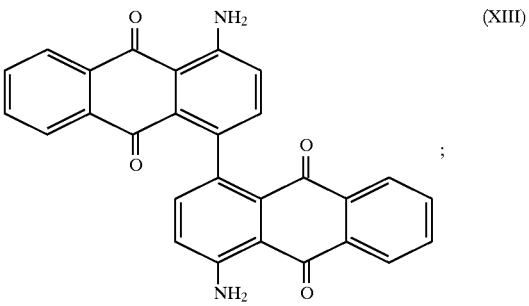

and ix) phthalocyanines of the formula

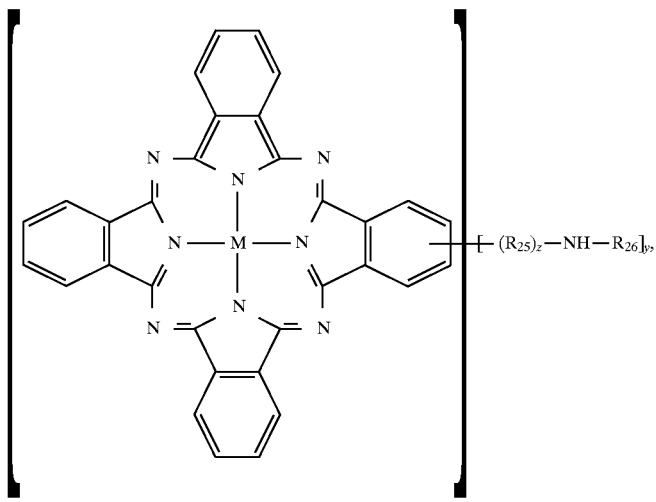

(XIV)

in which
M is $H_2$, Zn, Cu, Ni, Fe, TiO or VO,
$R_{25}$ is —CH($R_{27}$)— or —$SO_2$—,
$R_{26}$ is hydrogen, $C_1$–$C_4$alkyl, —$NHR_{27}$, —$NHCOR_{28}$, —$COR_{28}$ or

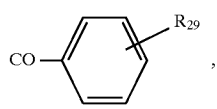

$R_{27}$ is hydrogen or $C_1$–$C_4$alkyl,
$R_{28}$ is $C_1$–$C_4$alkyl, $R_{29}$ is hydrogen, halogen, $C_1$–$C_4$alkyl or $C_1$–$C_4$alkoxy,
z is 0 or 1 and
y is a number from 1 to 4.

24. A process of claim 1, wherein the substituents are selected from the group consisting of halogen, nitro, amino, hydroxyl, $C_1$–$C_{18}$alkyl, $C_5$–$C_6$cycloalkyl, $C_1$–$C_4$alkoxy, $C_1$–$C_{18}$alkylthio, $C_1$–$C_{18}$alkylamino, $C_2$–$C_{18}$dialkylamino or $C_1$–$C_{18}$cycloalkylamino and are attached to the carbon framework via a direct bond or via carbonyl, carbonyloxy, oxycarbonyl, sulfonyl or sulfinyl.

* * * * *